(12) United States Patent
Kober et al.

(10) Patent No.: US 6,376,425 B1
(45) Date of Patent: *Apr. 23, 2002

(54) SYNERGISTIC GROWTH-REGULATING MIXTURE

(75) Inventors: Reiner Kober, Fussgönheim; Karl-Heinrich Schneider, Kleinkarlb; Hans Ziegler, Mutterstadt; Mary Elizabeth Callan, Limburgerhof, all of (DE); Charles W. Finch, Garner, NC (US); Reinhold Stadler, Kirrweiler (DE); Peter Hofmeister, Neustadt (DE); Wilhelm Rademacher, Limburgerhof (DE); Elmar Kibler, Hassloch (DE); Reimer Göttsche, Baden-Baden (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/175,284

(22) Filed: Oct. 20, 1998

Related U.S. Application Data

(60) Provisional application No. 60/063,186, filed on Oct. 20, 1997.

(51) Int. Cl.⁷ .............................................. A01N 25/00
(52) U.S. Cl. ................................................... 504/116.1
(58) Field of Search ................................ 504/248, 345, 504/116.1

(56) References Cited

U.S. PATENT DOCUMENTS

| | | | |
|---|---|---|---|
| 4,525,200 A | 6/1985 | Kimpara et al. | 71/76 |
| 4,693,745 A | 9/1987 | Brunner | 71/94 |
| 4,744,811 A | 5/1988 | Schulz et al. | 71/68 |
| 4,808,213 A | * 2/1989 | Schmierer | 71/92 |
| 5,455,220 A | 10/1995 | Dedolph | 504/241 |
| 5,510,321 A | * 4/1996 | Hirabayashi | 504/289 |

FOREIGN PATENT DOCUMENTS

| | | |
|---|---|---|
| CA | 2 193 873 | 6/1997 |
| EP | 0 243 834 | 4/1987 |
| EP | 0 344 533 | 12/1989 |
| EP | 0 434 613 A2 | 12/1990 |
| EP | 0 573 177 A2 | 5/1993 |
| WO | WO 96/00005 | 6/1995 |

OTHER PUBLICATIONS

Chemical Abstracts, vol. 80, No. 11, 1974, Abstract No. 56466, XP–002097015, "Plant Growth Regulator Containing Ethylene Glycol And A Mineral Acid".
Database WPI, AN 73–77478U, XP 002097016; "Plant Growth Regulate Composition Benyzl Alcohol Compound Active Ingredient".

* cited by examiner

Primary Examiner—José G. Dees
Assistant Examiner—Konata M George
(74) Attorney, Agent, or Firm—Merchant & Gould P.C.

(57) ABSTRACT

The invention provides novel mixtures of quaternary ammonium salts having plant growth-regulating properties. The salts, as well as other active ingredients used to regulate plant growth, are dissolved in solvents having either formula II(a) or II(b), as depicted below:

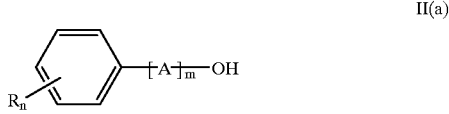

II(a)

or

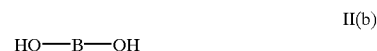

II(b)

wherein
"R" is Hydrogen or a $C_1$–$C_{18}$ alkyl,
"n" is 0, 1,2 or 3,
"A" is a $C_1$–$C_6$ alkene or a $C_1$–$C_6$ oxyalkylene,
"m" is 1, 2, 3, 4 or 5, and
"B" is a straight-chain or branched $C_2$–$C_8$ alkylene.

15 Claims, No Drawings

SYNERGISTIC GROWTH-REGULATING MIXTURE

This application claim benefit to Provisional No. 60/063,186 filed Oct. 20, 1997.

FIELD OF THE INVENTION

The present invention relates to novel mixtures having growth-regulating properties and more specifically relates to a novel growth regulating mixture of quaternary ammonium salts with growth regulating active ingredients in a suitable solvent. The invention further relates to methods for regulating plant growth.

BACKGROUND OF THE INVENTION

Plant growth regulators ("Plant Growth Regulators") serve many useful purposes in the areas of crop cultivation, agriculture and gardening. For instance, a particular concern in cultivating such crops as grain, corn, sunflowers and soybeans, is the problem of lodging of the plants due to unfavorable weather conditions prior to harvest. Inhibiting the longitudinal growth of the plants results in a thicker, stronger stem, thereby reducing the risk of lodging. Also, by inhibiting longitudinal growth of cotton crops, the course of maturation can be controlled in order to permit completely mechanized harvesting.

Growth regulation of fruit trees can result in reduced trimming costs, while also enabling the grower to restrict annual fluctuations in fruit tree yield.

Some Plant Growth Regulators can also be used to control the susceptibility of crops to adverse weather conditions by improving frost resistance. This is particularly useful in winter grain. Excess longitudinal growth and the development of overly lush leaves results in a more frost-vulnerable plant. It is also desirable to inhibit growth even during favorable growing conditions for example after sowing and before winter frosts begin. This results in a plant that is less vulnerable to frost. In addition to increased frost resistance, the relatively small leaf and plant mass become less susceptible to diseases such as fungus. Regulating growth of crop plants also enables many crop plants to be planted closer together resulting in a higher yield from a given area.

Quaternary ammonium salts, such as mepiquat chloride and chloromequat chloride, whose formulas are depicted below, are known Plant Growth Regulators.

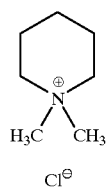

Mepiquat Chloride

I(a)

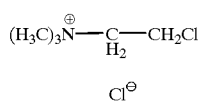

Chloromequat Chloride

I(b)

These compounds are commercially available in aqueous concentrates or in tablet or granule form (e.g. PIX® plant growth regulator, BASF Corporation). These compounds can be made by methods known in the art, such as, by converting secondary or tertiary amines with methyl halides. A method for water-free preparation of mepiquat chloride, which can be used as a solid charge stock in formulations, is described in European Patent Application, Publication No. 0 573 177 A2, incorporated herein by reference.

Other known active ingredients having growth regulating properties are described in European Patent Application, Publication No. 0 243 834 A2 and include the following formula:

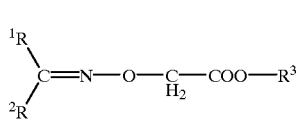

III

In this formula, the radicals have the following meanings: $R^1$ and $R^2$ independently of one another may be hydrogen, $C_1$–$C_6$ alkyl, $C_1$–$C_6$ halogen alkyl, $C_1$–$C_4$ alkoxy-$C_1$–$C_6$ alkyl, $C_3$–$C_6$ alkenyl and phenyl, which may be unsubstituted or may carry one or independently of one another two or three of the following groups—nitro, chloro, fluoro, $C_1$–$C_3$ alkyl, $C_1$–$C_3$ haloalkyl, and methylene dioxy; or $R^1$ and $R^2$ together with the carbon atom to which they are bonded form a 5- to 7-member ring, which in turn may carry one or independently of one another two $C_1$–$C_3$ alkyl groups; $R^3$ may be hydrogen, a cation suitable for agriculture, $C_1$–$C_8$ alkyl, $C_3$–$C_7$ cycloalkyl, $C_1$–$C_4$ alkyloxy, $C_1$–$C_6$ alkyl, a $CH_2$—$C(O)$—$OR^4$ group, wherein $R^4$ stands for $C_1$–$C_8$ alkyl, $C_3$–$C_7$ cycloalkyl, $C_1$–$C_4$ alkyloxy-$C_1$–$C_6$ alkyl, hydrogen or a cation suitable for agriculture.

Other active ingredients that have been described as possessing growth regulating properties include acylcyclohexadiones for example those described in U.S. Pat. No. 4,560,403, incorporated herein by reference, as represented by the formula:

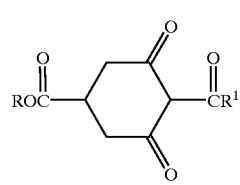

IV wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound.

A specific compound for use as a growth regulating compound is prohexadione represented by the formula:

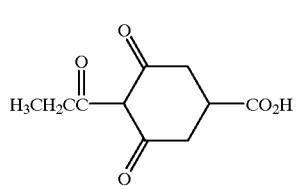

IV(a)

As used herein, prohexadione includes the compound (IUPAC name) 3,5-dioxo-4-propionylcyclohexanecarboxylic acid (or 3,5-dioxo-4-(1-oxopropyl)cyclohexanecarboxylic acid (C.A. name)) and also 3-hydroxy-4-prionyl-5-oxo-3-cyclohexene carboxylic acid and its pharmacological effective salts for example a chloride, sulfate, metrab, acetate, carbonate, hydride, hydroxide, sodium, potassium, calcium, magnesium, barium, aluminum, nickel, copper, manganese, cobalt zinc, iron or silver.

Other acylcyclohexadione compounds having growth regulating properties are described in U.S. Pat. No. 4,693,745, incorporated herein by reference, and are represented by the formula:

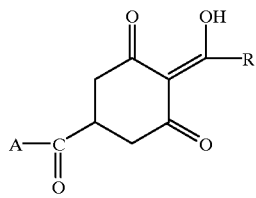

V wherein
A is an $-OR_2$ or $-NR_3R_4$ radical,
R is $C_3$–$C_6$ cycloalkyl,
$R_2$ $R_3$ and $R_4$ are each independently hydrogen, $C_1$–$C_6$alkyl, $C_1$–$C_6$haloalkyl, $C_2$–$C_{10}$alkoxyalkyl, $C_2$–$C_{10}$alkylthioalkyl, $C_3$–$C_6$alkenyl, which is unsubstituted or substituted by halogen, $C_1$–$C_4$alkoxy or $C_1$–$C_4$alkylthio; $C_3$–$C_6$alkynyl; phenyl or $C_1$–$C_6$aralkyl, wherein the phenyl nucleus is unsubstituted or substituted by halogen, $C_1$–$C_4$alkyl, $C_1$–$C_4$alkoxy, $C_1$–$C_4$haloalkyl, nitro or cyano; one of $R_3$ and $R_4$ is methoxy; or
$R_3$ and $R_4$, together with the nitrogen atom to which they are attached, form a 5- or 6-membered heterocyclic ring system which may contain an additional oxygen or sulfur atom in the ring; and the metal or ammonium salts thereof.

Specific compounds of the immediately above noted formula include trinexapac (IUPAC name 4-cyclopropyl(hydroxy)methylene-3,5-dioxyocyclohexanecarboxylic acid) and preferably its ethyl ester, trinexapac-ethyl (IUPAC name, ethyl 4-cyclopropyl(hydroxy)methylene-3,5-dioxocyclohexanecarboxylate; CA name, ethyl 4-(cyclopropylhydroxymethylene)-3,5-dioxocyclohexanecarboxylate) represented by the formula:

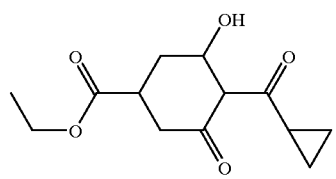

V(a)

Mixtures of active ingredients with quaternary ammonium salts, such as those of formulations I(a) and I(b), are discussed in European Patent Application, Publication No. 0 434 613 A2. Although there mixture provide useful and beneficial properties, superior stability properties are sought for mixtures of active ingredients.

It is therefore an object of the present invention to create a formulation having growth regulating properties by combining the salt-like active ingredients of formulas I(a) and/or I(b), in a solution while simultaneously maintaining stability of the active ingredients. Another object of the present invention is to obtain growth-regulating properties by combining ingredients of formulas I(a) and/or I(b), with active ingredients of formulas III or with a acylcyclohexadione, and maintain the stability of the active ingredients.

SUMMARY OF THE INVENTION

The present invention provides formulations in which salt-like active ingredients, such as the quaternary ammonium salts of formulas I(a) and I(b), are dissolved in suitable organic solvents, in which other active ingredients with growth regulating properties, such as those of formula III, IV or V, can also be added while maintaining adequate stability of the active ingredients. While it is known that salt-like active ingredients such as quaternary ammonium salts are soluble in water, due to their polar, salt-like and inorganic characteristics, such aqueous solutions may cause degradation of other active ingredients used in growth regulating mixtures.

It has been found, surprisingly, that the salt-like formulations I(a) and I(b) are suitably soluble in organic solvents having either of the following two formulas which are referred to herein as formulas II(a) and II(b) respectively:

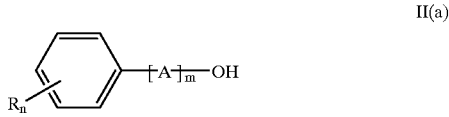

II(a)

or

II(b)

wherein
"R" is Hydrogen or a $C_1$–$C_{18}$ alkyl,
"n" is 0, 1, 2 or 3,
"A" is a $C_1$–$C_6$ alkene or a $C_1$–$C_6$ oxyalkylene,
"m" is 1, 2, 3, 4 or 5, and
"B" is a straight-chain or branched $C_2$–$C_8$ alkylene.

While these solvents provide adequate solubility of salt-like active ingredients of formulas I(a) and/or I(b), they also are good solvents for active ingredients of formulas III, IV and V. Moreover, use of these solvents has been found to result in very good stability of active ingredients in solution. Particular advantage may be found by combining the salt-like active ingredients of formulas I(a) and or I(b) in combination with compounds of formulas III, IV and/or V. Growth regulating properties are attained and the mixtures adequately sustain the stability of the active ingredients. These formulations are preferably provided in the substantial absence of water.

DETAILED DESCRIPTION OF THE INVENTION

Preferred embodiments of the invention include mixtures comprising quaternary ammonium salts of formulations I(a) and/or I(b) in the amount from 1–50% by weight, preferably 2–30% by weight, and in particular 3–25% by weight of the mixture.

The solvents of formula II(a) may comprise derivatives of aromatic alcohols or ethers. Aromatic alcohols are preferred in which the OH group is bonded to the aromatic ring via an alkylene group having from 1 to 4 Carbon atoms or an oxyalkylene group having from 2 to 6 Carbon atoms. In some cases, benzyl alcohol, ethylene glycol monophenylether, propylene glycol monophenylether, butylene glycol monophenylether and the derivatives thereof, substituted in the aromatic ring with 1 to 3 $C_1$–$C_3$ alkyl groups, have been said to be particularly advantageous.

The solvents of formula II(b) may comprise linear or branched diols with a $C_2$–$C_8$ alkylene chain. The two hydroxy groups can be located either at the end or inside the chain. Preferred representatives of the solvents of formula II(b) are propylene glycol and butylene glycol. By comparison, the stability of the active ingredients in those solvents is somewhat better than in ethylene glycol.

The amount of solvents of formulas II(a) and/or II(b) in the formulation of the invention is preferably provided in the range of from 20–99% by weight, preferably from 35–98% by weight, and particularly from 50–96% by weight, with reference to the total weight of the formulation.

The formulation can also have from 0–60% by weight, preferably 1–50% by weight and particularly 2–35% by weight of further active ingredients. Active ingredients such as those having formulas III, IV, and or V III(b) are known. For example, compounds of formula III are described generally in PCT Application WO 96/00005. Their effect in reducing the endogenous ethylene content in higher-order plants is described for instance in German Patent Disclosures DE 36 13 649, DE 41 06 509 and U.S. Pat. No. 4,744,811.

An active ingredient for use in the present invention is represented by Formula IV(a) an example of which a prohexandione.

One preferred active ingredient is represented Formula V(a) and a preferred example of which is trinexapac-ethyl.

With reference to formula III, instead of the free acids their agricultural acids may also be present. In general the type of salt does not matter. Typically the salts of those bases that do not negatively affect the action of the compounds of formulas III, IV and V. As basic salts, those that are especially suitable are those of alkaline metals, preferably the salts of sodium and potassium, the salts of alkaline earth metals, preferably calcium, magnesium, copper, zinc and iron salts, and the ammonium salts, which can have from 1 to 3 $C_1$–$C_4$ alkyl substitutes and/or a phenyl or benzyl substitute, preferably diisopropyl ammonium, tetramethyl ammonium, tetrabutyl ammonium, trimethylbenzyl ammonium, and trimethyl-(2-hydroxyethyl) ammonium salts, the phosphonium salts, the sulfonium salts, preferably tri-($C_1$–$C_4$-)alkyl sulfonium salts, and the sulfoxonium salts, preferably tri-($C_1$–$C_4$-)alkyl sulfoxonium salts.

Preferred active ingredients having the formula set forth as formula III are compounds having the following combinations of radicals:

(1) the $R^1$ and $R^2$ radicals are $C_1$–$C_6$ alkyls, such as methyl, ethyl, propyl, or the $R^1$ and $R^2$ radicals, together with the Carbon to which they are bonded form a 5- to 7-member ring, such as cyclopentylidine or cyclohexylidine;

(2) the $R^3$ radical is hydrogen, a $C_1$–$C_6$ alkyl group, or a $CH_2$—$C(O)OR^4$ group; and (3) the $R^4$ radical is hydrogen or a $C_1$–$C_6$ alkyl group.

Other preferred active ingredients of formulation III(a) are those listed below and designated as formulas III(a)–III(d):

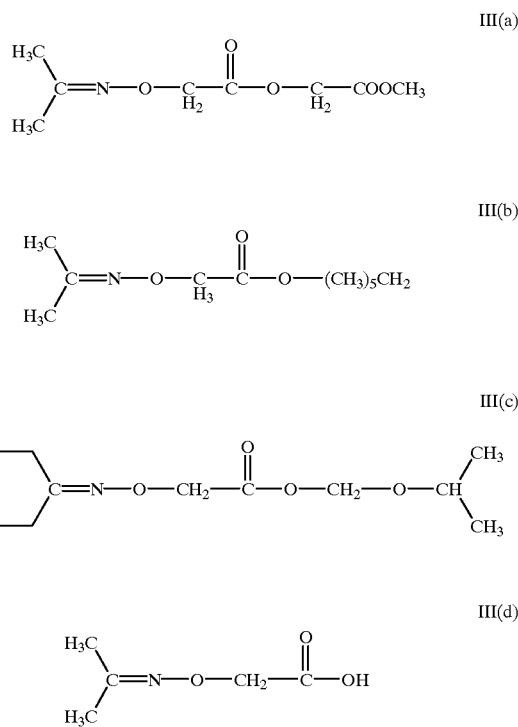

and the acids on which they are based and their alkali, alkaline earth or ammonium salts.

The mixtures of the present invention can also have, as components up to 30 percent by weight and preferably up to 20 percent by weight, further formulation adjuvants, of the kind known to one skilled in the art such as, for example, the adjuvants named in European Patent Disclosure EP A 434 613 and incorporated herein by reference.

When surface-active substances are used as further formulation adjuvants, the substances that can be considered are the alkali, alkaline earth and ammonium salts of aromatic sulfonic acids, such as lignin-, phenol-, naphthalene-, and dibutylnaphthalenesulfonic acid, as well as those of fatty acids, alkyl and alkylaryl sulfonates, alkyllaurel ether and fatty alcohol sulfates, and salts of sulfated hexa-, hepta- and octadecanols or fatty alcohol glycol ethers, condensation products of sulfonated naphthalene and its derivatives with formaldehyde, condensation products of naphthalene or naphthalenesulfonic acids with phenol and formaldehyde, polyoxyethylene octyl phenol ether, ethoxylated isooctyl, octyl or nonylphenol, alkylphenol or tributylphenyl polyglycol ether, alkylaryl polyether alcohols, isotridecyl alcohol, fatty alcohol ethylene oxide condensates, ethoxylated castor oil, polyoxyethylene alkyl ether or polyoxypropylene, lauryl alcohol polyglycol ether acetate, sorbitol ester, lignin sulfite waste liquors, or methylcellulose.

The formulations according to the invention can be prepared in a manner known by those ordinarily skilled in the art such as by adding compounds of formulas I(a) and/or I(b), and active ingredients of formulas III, IV and/or V and other formulation adjuvants into the organic solvents of formulas II(a) and/or II(b), while stirring and, optionally, while heating.

The preferred use of the formulations according to the invention is to treat plants at preemergence or at the postemergence stage with an effective amount of the formulation on the basis of active ingredients of formulas I(a) and/or I(b), or the mixtures of these active ingredients of formulas I(a) and/or I(b) with ingredients of formulas III, IV and/or V. Seed dressing is also another possible use of the present invention.

Depending on the season, the target crops, and the stage of growth, the quantities of mixture applied may range from 0.0001 to 1.0, preferably 0.001 to 0.5, and especially 0.001 to 0.1 kg/ai/ha.

The mixtures may effect practically all development stages of a plant in various ways and are therefore used as growth regulators. The versatility of action depends on the following factors:

(a) the species and variety of plant;

(b) the timing of the application, with respect to the development stage of the plant and the season of the year;

(c) the application site and application method (such as, seed dressing, soil treatment, leaf application or in tree trunk injection);

(d) climatic factors, such as temperature, amount of precipitation, and also length of day and intensity of light;

(e) soil property, including fertilization, (f) the concentrations used of the active substances I(a) and/or I(b) and III(a) and/or III(b).

From among the numerous uses of the mixtures of the present invention, and agents containing them, in crop cultivation, in agriculture and in gardening, several are mentioned below.

With these mixtures and agents, the vegetative growth of the plants can be sharply inhibited, which is expressed as a reduction in longitudinal growth. Hence, the treated plants exhibit a dwarfed growth and a darker leaf coloration.

Furthermore, the mixtures according to the invention can cause a reduction in endogenous ethylene formation in the treated plants. This leads to a retardation of senescence phenomena and can thus prolong the life of cut flowers and lengthen the assimilation phase of crop plants and bring about increased harvest yields;

a reduction or at least temporary delay in dropping of leaves, blossoms and fruit;

an improvement in the formation of root nodules in leguminous plants and hence more-intensive assimilation of nitrogen from the air;

a reduced sensitivity to stress situations (such as lack of water, low temperatures, mechanical strain, attach by harmful fungi or insects).

Also, with the mixtures of the present invention, increased yields of both plant parts and plant ingredient substances can be attained. It is thus possible for instance to induce the growth of greater amounts of buds, blossoms, leaves, fruits, seed grains, roots and nodes, to increase the sugar content in sugar beets, cane sugar and citrus fruits, to increase the protein content of grain or soybeans, or to increase the yield of cellulose fibers from cotton.

The mixtures of the present invention can also be used to bring about increases in yields by intervening in plant metabolism or by promoting or inhibiting vegetative and/or generative growth.

Also, with these mixtures, not only can the stages of development be shortened or lengthened, but the maturation of harvested plant parts, before or after the harvest, can be accelerated or delayed. Thus, for instance, a more-concentrated timing of cotton boll maturation can result in a greater ease of harvesting for the grower.

The consumption of water by plants can also be reduced by practicing the invention herein described. This is especially important for agricultural areas that require artificial irrigation at high expense, such as in arid or semiarid regions. The intensity of irrigation can be reduced by using the agents according to the invention, making farming less expensive. Under the influence of the agents:

the width to which the stomata open is reduced;

a thicker epidermis and cuticle are formed;

root proliferation in the soil is improved; and the microclimate in the planted fields is favorably affected by more-compact growth.

The mixtures can be supplied to the crop plants both from seed (as a seed dressing agent) or via the soil, that is, through the roots, and preferably by spraying the shoots. Given the versatility of application methods, the mixtures can be used in a great number of crop plants.

In preparing the mixtures, one preferably uses the pure active ingredients of formulas I(a) and/or I(b) and of formulas III, IV and/or V, to which other active ingredients can be added, such as active ingredients that regulate plant growth, herbicidal active ingredients, and active ingredients that protect against harmful fungi or animal pests, or fertilizers.

The examples set forth below establish he solubility of salt-like active ingredients, such as those of formulas I(a) and I(b), and the stability of active ingredients, such as those of formulas III, IV and V, in solvents such as those of formulas II(a) and II(b). Specifically, Examples 1–14, as set forth below in Table 1, show the solubility of mepiquat chloride in various solvents. Fifteen percent by weight of mepiquat chloride was added to 100 grams of each solvent and it was observed whether complete dissolution occurred.

TABLE 1

| Example No. | Solvent | Solubility of 15 weight % Solution |
|---|---|---|
| 1V | Water | soluble |
| 2V | Isopropyl* | soluble |
| 3V | Ethylene glycol | soluble |
| 4V | Propylene carbonate | insoluble |
| 5V | n-Octylpyrrolidone | insoluble |
| 6V | Cyclohexanone | insoluble |
| 7V | Diethylene glycol dimethyl ether | insoluble |
| 8V | Ethylene glycol monobutyl ether | insoluble |
| 9V | Dipropylene glycol | insoluble |
| 10V | 1-Nonanol | insoluble |
| 11V | 1-Tridecanol | insoluble |
| 12V | Cyclohexanol | insoluble |
| 13V | Cyclohexylmethanol | insoluble |
| 14 | Benzyl alcohol | soluble |
| 15 | Ethylene glycol monophenylether | soluble |
| 16 | Propylene glycol monophenylether | soluble |
| 17 | Propylene glycol | soluble |

V= Comparison experiment
*= Generally, because of their low boiling and flash points, isopropanol and short-chain alcohols are less suitable for the formulation of plant pesticides.

A particularly surprising finding, as shown in Table 1 is the solubility of the active ingredient mepiquat chloride in benzyl alcohol (example 14) in comparison to cyclohexylmethanol (example 13V). Due to the cycloaliphatic ring structure similar to that of the active ingredient, one skilled in the art would have expected better solubility in cyclohexylmethanol, rather than in benzyl alcohol.

The stability of the active ingredient of formula III where $R^1$ and $R^2$ are methyl and $R^3$ is $CH_2COOCH^3$ in various solvents is set forth below in examples 18–24, shown in Table 2. In order to determine stability, solutions containing ten percent by weight of each ingredient were stored at a temperature of 54° C. for 14 days, and the residual active ingredient content, calculated in percent of the original content, was then determined by HPLC analysis.

TABLE 2

| Example No. | Solvent | Residual active ingredient content (%) |
|---|---|---|
| 18 | Water** | <<0.1 |
| 19 | Ethylene glycol | 80.2 |
| 20 | Cyclohexanol | 99.7 |
| 21 | Propylene glycol | 95.2 |
| 22 | Benzyl alcohol | 96.5 |
| 23 | Ethylene glycol monophenylether | 99.5 |
| 24 | Propylene glycol monophenylether | 100.0 |

**For reasons of solubility, active ingredient content is only 4%.

These examples show that very good stability of the active ingredients is achieved when they are dissolved in solvents of the present invention.

In examples 25–29, mixture formulations according to the invention were prepared, with various solvents. The solutions contained 5 percent by weight of the active ingredient mepiquat chloride and the active ingredient used in examples 18–24. The stability of the active ingredients was determined as described above for Examples 18–24. The results are found in Table 3:

TABLE 3

| Experiment No. | Solvent | Residual active ingredient content (in % of the active ingredient of formula III(a) |
|---|---|---|
| 25 | Ethylene glycol | 63.8 |
| 26 | Propylene glycol | 91.8 |
| 27 | Benzyl alcohol | 98.8 |
| 28 | Ethylene glycol monophenylether | 99.4 |
| 29 | Propylene glycol monophenylether | 99.8 |

These examples confirm that by using the solvents selected from formulations II(a) and/or II(b), combination formulations can be prepared that on the one hand are adequate solvents of active ingredients that are salt-like active polar, and more inorganic in character. Moreover, such formulations permit the addition of active ingredients selected from formulas III, IV and/or V with active ingredients of formula I(a) and/or I(b), while not deleteriously lessening the stability of active ingredients III, IV and/or V.

The invention has been described in considerable detail with reference to its preferred embodiments. However, numerous variations and modifications can be made within the spirit and scope of the invention without departing from the invention as described in the foregoing specification and defined in the appended claims.

We claim:

1. A formulation for use in plant growth regulation comprising:

(a) quaternary ammonium salt having a formula of I(a) or I(b)

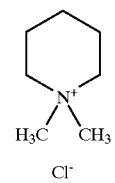

Cl⁻

Mepiquat Chloride

I(a)

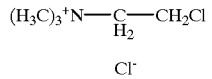

Cl⁻

Chloromequat Chloride

I(b)

and (b) solvent having formula II(a)

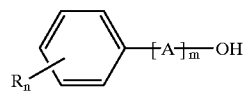

II(a)

wherein
R is hydrogen or $C_1$–$C_{18}$ alkyl,
n is 0, 1, 2, or 3,
A is $C_2$–$C_6$ alkylene or $C_2$–$C_6$ oxyalkylene, and
m is 1, 2, 3, 4, or 5,
wherein said formulation is a solution of said quaternary ammonium salt in said solvent and is provided in the substantial absence of water.

2. The formulation of claim 1, wherein formula II(a) m is 1.

3. The formulation according to claim 1 comprising from about 1 percent by weight to about 50 percent by weight, based on the total weight of said formulation, one or more quaternary ammonium salts.

4. The formulation according to claim 1 comprising from about 2 percent by weight to about 30 percent by weight, based on the total weight of said formulation, one or more quaternary ammonium salts.

5. The formulation according to claim 1 comprising from about 3 percent by weight to about 25 percent by weight based on the total weight, of said formulation, one or more quaternary ammonium salts.

6. The formulation according to claim 1 comprising from about 20 percent by weight to about 99 percent by weight, based on the total weight of said formulation, one or more solvents.

7. The formulation according to claim 1 comprising from about 35 percent by weight to about 98 percent by weight, based on the total weight of said formulation, one or more solvents.

8. The formulation according to claim 1 comprising from about 50 percent by weight to about 96 percent by weight, based on the total weight of said formulation, one or more solvents.

9. A formulation for use in plant growth regulation comprising:
(a) one or more solvents having a formula II(a):

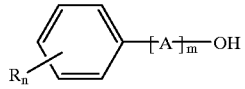

II(a)

wherein
R is hydrogen or $C_1$–$C_{18}$ alkyl,
n is 0, 1, 2, or 3,
A is $C_2$–$C_6$ alkylene or $C_2$–$C_6$ oxyalkylene,
m is 1, 2, 3, 4, or 5; and
(b) an active ingredient(s) for regulating plant growth having a formula III, IV, or V:

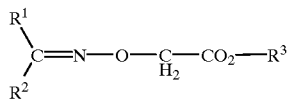

III wherein
$R^1$ and $R^2$ are independently hydrogen, $C_1$–$C_6$ alkyl, $C_1$–$C_6$ halogen alkyl, $C_1$–$C_4$ alkoxy-$C_1$–$C_6$ alkyl, $C_3$–$C_6$ alkenyl and phenyl, which may be unsubstituted or may carry one or, independently of one another, two or three of the following groups: nitro, halogen, $C_1$–$C_3$ alkyl, $C_1$–$C_3$ haloalkyl, and $C_1$–$C_4$ alkylene dioxy; or $R^1$ and $R^2$ together with the carbon atom to which they are bonded form a 5- to 7-member ring, which in turn may carry one or independently of one another two $C_1$–$C_3$ alkyl groups;
$R^3$ is hydrogen, a cation suitable for agriculture, $C_1$–$C_8$ alkyl, $C_3$–$C_7$ cycloalkyl, $C_1$–$C_4$ alkyloxy-$C_1$–$C_6$ alkyl, or a $CH_2$—$C(O)$—$OR^4$ group; and
$R^4$ is hydrogen, a cation suitable for agriculture, $C_1$–$C_8$ alkyl, $C_3$–$C_7$ cycloalkyl, or $C_1$–$C_4$ alkyloxy-$C_1$–$C_6$ alkyl;

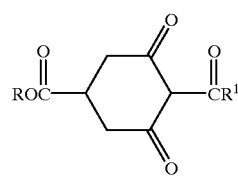

IV wherein
R is hydrogen, an alkyl group, an alkylthioalkyl group, or an unsubstituted or substituted phenyl group; and $R^1$ is an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound; and

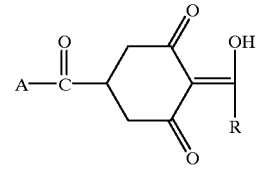

V wherein
A is an —$OR_2$ or —$NR_3R_4$ radical,
R is a $C_3$–$C_6$ cycloalkyl, and
$R_2$, $R_3$ and $R_4$ are each independently hydrogen, $C_1$–$C_6$ alkyl, $C_1$–$C_6$ haloalkyl, $C_2$–$C_{10}$ alkoxyalkyl, $C_2$–$C_{10}$ alkylthioalkyl, $C_3$–$C_6$ alkenyl, which is unsubstituted or substituted by halogen, $C_1$–$C_4$ alkoxy or $C_1$–$C_4$ alkylthio; $C_3$–$C_6$ alkynyl; phenyl or $C_1$–$C_6$ aralkyl, wherein the phenyl nucleus is unsubstituted or substituted by halogen, $C_1$–$C_4$ alkyl, $C_1$–$C_4$ alkoxy, $C_1$–$C_4$ haloalkyl, nitro or cyano; one of $R_3$ and $R_4$ is methoxy; or $R_3$ and $R_4$, together with the nitrogen atom to which they are attached, form a 5- or 6-membered heterocyclic ring system which may contain an additional oxygen or sulfur atom in the ring; and the metal or ammonium salts thereof;
wherein said formulation is a solution of said active ingredient in said solvent and is provided in the substantial absence of water.

10. The formulation of claim 9, wherein formula II(a) m is 1.

11. The formulation according to claim 9 further comprising a quaternary ammonium salt.

12. A method for regulating plant growth comprising applying the formulation according to claim 1 to seeds, plants or soil.

13. The method of claim 11, wherein said formulation is applied at a rate of from about 0.0001 kg/ha to about 1.0 kg/ha.

14. The method of claim 11, wherein said formulation is applied at a rate of from about 0.001 kg/ha to about 0.5 kg/ha.

15. The method of claim 11, wherein said formulation is applied at a rate of from about 0.001 kg/ha to about 0.1 kg/ha.

* * * * *

UNITED STATES PATENT AND TRADEMARK OFFICE
CERTIFICATE OF CORRECTION

PATENT NO. : 6,376,425 B1
DATED : April 23, 2002
INVENTOR(S) : Kober et al.

It is certified that error appears in the above-identified patent and that said Letters Patent is hereby corrected as shown below:

<u>Title page,</u>
Item [75], Inventors, city for Karl-Heinrich Schneider should read -- Kleinkarlbach -- rather than "Kleinkarlb"

<u>Column 8,</u>
Table 1, line 43, "Solubiiity" should read -- Solubility --
Line 61, "iow" should read -- low --

<u>Column 9,</u>
Line 8, insert -- active -- after "weight of each"

<u>Column 12,</u>
Line 43, "The method of claim 11" should read -- The method of claim 12 --
Line 46, "The method of claim 11" should read -- The method of claim 12 --
Line 49, "The method of claim 11" should read -- The method of claim 12 --

Signed and Sealed this

Twelfth Day of November, 2002

*Attest:*

JAMES E. ROGAN
*Attesting Officer*     *Director of the United States Patent and Trademark Office*